United States Patent
Huang et al.

(10) Patent No.: US 11,260,380 B2
(45) Date of Patent: *Mar. 1, 2022

(54) IMINES WITH TUNABLE NUCLEOPHILICITY AND STERIC PROPERTIES THROUGH METAL COORDINATION: APPLICATIONS AS LIGANDS AND METALLOORGANOCATALYSTS

(71) Applicant: King Abdullah University of Science and Technology, Thuwal (SA)

(72) Inventors: Kuo-Wei Huang, Thuwal (SA); Qianyi Zhao, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 0 days.

This patent is subject to a terminal disclaimer.

(21) Appl. No.: 16/458,500

(22) Filed: Jul. 1, 2019

(65) Prior Publication Data
US 2019/0321812 A1    Oct. 24, 2019

Related U.S. Application Data

(62) Division of application No. 15/510,119, filed as application No. PCT/IB2015/056894 on Sep. 9, 2015, now Pat. No. 10,399,072.
(Continued)

(51) Int. Cl.
*B01J 31/18* (2006.01)
*C07F 9/58* (2006.01)
(Continued)

(52) U.S. Cl.
CPC ......... *B01J 31/189* (2013.01); *B01J 31/0201* (2013.01); *B01J 31/0212* (2013.01); *B01J 31/0237* (2013.01); *B01J 31/0274* (2013.01); *B01J 31/12* (2013.01); *B01J 31/2295* (2013.01); *B01J 37/04* (2013.01); *C07C 29/09* (2013.01); *C07C 29/14* (2013.01); *C07C 29/15* (2013.01); *C07C 231/10* (2013.01); *C07D 317/36* (2013.01); *C07F 9/58* (2013.01);
(Continued)

(58) Field of Classification Search
None
See application file for complete search history.

(56) References Cited

U.S. PATENT DOCUMENTS

| | | | |
|---|---|---|---|
| 8,598,351 | B2 | 12/2013 | Huang et al. |
| 2007/0117840 | A1 | 5/2007 | Itoh et al. |
| 2012/0323007 | A1 | 12/2012 | Huang et al. |

OTHER PUBLICATIONS

Ziolkowski et al. Polish J. Chem., 82, 1687-1694, (Year: 2008).*
(Continued)

*Primary Examiner* — Yun Qian
(74) *Attorney, Agent, or Firm* — Billion & Armitage

(57) ABSTRACT

The invention describes phospho-amino pincer-type ligands, metal complexes thereof, and catalytic methods comprising such metal complexes for conversion of carbon dioxide to methanol, conversion of aldehydes into alcohols, conversion of aldehydes in the presence of a trifluoromethylation agent into trifluorinated secondary alcohols, cycloaddition of carbon dioxide to an epoxide to provide cyclic carbonates or preparation of an amide from the combination of an alcohol and an amine.

6 Claims, 2 Drawing Sheets

Complex 3 of Scheme 6

Related U.S. Application Data

(60) Provisional application No. 62/049,022, filed on Sep. 11, 2014.

(51) Int. Cl.

| | | |
|---|---|---|
| *C07F 15/04* | (2006.01) | |
| *B01J 31/12* | (2006.01) | |
| *C07C 29/09* | (2006.01) | |
| *C07C 29/14* | (2006.01) | |
| *C07C 29/15* | (2006.01) | |
| *C07C 231/10* | (2006.01) | |
| *C07D 317/36* | (2006.01) | |
| *B01J 31/22* | (2006.01) | |
| *B01J 31/02* | (2006.01) | |
| *B01J 37/04* | (2006.01) | |

(52) U.S. Cl.
CPC ............ *C07F 15/04* (2013.01); *C07F 15/045* (2013.01); *B01J 2231/323* (2013.01); *B01J 2231/341* (2013.01); *B01J 2231/342* (2013.01); *B01J 2231/625* (2013.01); *B01J 2231/763* (2013.01); *B01J 2531/0244* (2013.01); *B01J 2531/821* (2013.01); *B01J 2531/847* (2013.01); *Y02P 20/52* (2015.11)

(56) References Cited

OTHER PUBLICATIONS

Qu et al. JACS, 136, 4974-4991 (Year: 2014).*
Database CA [Online], Chemical Abstracts Service, Columbus, Ohio, US; Schirmer, W., et al., Preparation, Properties, and Molecular Structures of a Rigid Tridentate Chelate Ligand N,N'-bis(Diphenylphosphino)-2,6-Diaminopyr Idine with MII and MO Transition.
Database CA {Online} Chemical Abstracts Service, Columbus, Ohio, US; Floerke, U., et al., "Crystal Structure of [N,N'-bis(Diphenylphosphino)2,6-Diaminopridine] Iodonickel (II) Iodide, (C5NH3) (P(C6H5)2(NH)2(INi)!,"XP002778186, retrieved from STN, Database.
Extended European Search Report in related European Application No. 15840786.6, dated Mar. 9, 2018.
Search Report and Written Opinion for PCT/IB2015/056894, dated Dec. 10, 2015.
Barbarini, et al., "Cycloaddition of CO2 to epoxides over both homogeneous and silica-supported guanidine catalysts", Tetrahedron Letters, 2003, 2931-2934.
Benito—Garagorri, et al., "Achiral and Chiral Transition Metal Complexes with Modularly Designed Tridentate PNP Pincer-Type Ligands Based on N-Heterocyclic Diamines", Organometallics, American Chemical Society, Jan. 22, 2006, 1900-1913.
Bugaut, et al., "Organocatalytic umpolung: N-heterocyclic carbenes and beyond", Chem Soc Rev, The Royal Society of Chemistry, 2012, 3511-3522.
Chakraborty,, et al., "Hydrosilylation of Aldehydes and Ketones Catalyzed by Nickel PCP-Pincer Hydride Complexes", Organometallics, 28, Dec. 31, 2008, 582-586.
Crabtree, "The Organometallic Chemistry of The Transition Metals", Fourth Edition, 2005, 1-552.
Dalko, et al., "In the Golden Age of Organocatalysis", Angew. Chem. Int. Ed., 2004, 5138-5175.
Enders, et al., "Organocatalysis by N-Heterocyclic Carbenes", American Chemical Society, 2007, 5606-5655.
Florke, et al., "Crystal structure of N,N'-bis(diphenylphosphino)-2,6-diaminopridine-iodo-nickel(II) iodide, (C5NH3)(P(C6H5)2(NH))2(INi)I", Zeitschrift fur Kristallographie 191, (1990), pp. 300-302.

Gaofeng, et al., "A Green Approach to Ethyl Acetate: Quantitative Conversion of Ethanol through Direct Dehydrogenation in a Pd—Ag Membrane Reactor", Chem. Eur. J., 2012, 15940-15943.
Gelman, et al., "Coordination Versatility of sp3-Hybridized Pincer Ligands toward Ligand-Metal Cooperative Catalysis", American Chemical Society, 2012, 2456-2466.
Ghosh, et al., "Simple RuCl3-Catalyzed Amide Synthesis from Alcohols and Amines", Eur. J. Org. Chem., 2010, 4266-4270.
Grondal, et al., "organocatalytic cascade reactions as a new tool in total synthesis", nature chemistry, Macmillan Publishers Limited, Mar. 2010, 167-178.
Gunanathan, et al., "Bond Activation by Metal-Ligand Cooperation: Design of "Green" Catalytic Reactions Based on Aromatization-Dearomatization of Pincer Complexes", Top Organomet Chem, 2011, 55-84.
Gunanathan, et al., "Metal—Ligand Cooperation by Aromatization—Dearomatization: A New Paradigm in Bond Activation and "Green" Catalysis", Accounts of Chemical Research, 2011, 588-602.
Heldebrant, et al., "The Reaction of 1,8-Diazabicyclo[5.4.0]undec-7-ene (DBU) with Carbon Dioxide", J. Org. Chem. 70, May 26, 2005, 5335-5338.
Ikariya, "Chemistry of Concerto Molecular Catalysis Based on the Metal/NH Bifunctionality", The Chemical Society of Japan, Dec. 18, 2010, 1-16.
Ishii, et al., "Organotransition—Metal Chemistry", Springer, 1975, 1-393.
Jurkauskas, et al., "Conjugate Reduction of r,â-Unsaturated Carbonyl Compounds Catalyzed by a Copper Carbene Complex", Organic Letter, vol. 5, No. 14, Jun. 19, 2003, 2417-2420.
Li-Peng, et al., "Efficient transfer hydrogenation reaction Catalyzed by a dearomatized PN3P ruthenium pincer complex under base-free Conditions", Journal of Organometallic Chemistry 700, 2012, 202-206.
Li-Peng, et al., "Enhanced Reactivities toward Amines by Introducing an Imine Arm to the Pincer Ligand: Direct Coupling of Two Amines To Form an Imine Without Oxidant", Organometallics, American Chemical Society, 2012, 5208-5211.
Milstein, "Discovery of Environmentally Benign Catalytic Reactions of Alcohols Catalyzed by Pyridine-Based Pincer Ru Complexes, Based on Metal-Ligand Cooperation", 2010, 915-923.
Mitton, et al., "Mild Reduction of Carbon Dioxide to Methane with Tertiary Silanes Catalyzed by Platinum and Palladium Silyl Pincer Complexes", Chem. Eur. J. 18,, Nov. 5, 2012, 15258-15262.
Park, et al., "An Efficient Iridium Catalyst for Reduction of Carbon Dioxide to Methane with Trialkylsilanes", J. Am. Chem. Soc. 134,, Jul. 5, 2012, 11404-11407.
Riduan, et al., "Conversion of Carbon Dioxide into Methanol with Silanes over N-Heterocyclic Carbene Catalysts", Angew. Chem. Int. Ed., 2009, 3322-3325.
Schirmer, et al., "Preparation, properties, and molecular structures of a rigid tridentate chelate ligand N,N'bis(diphenylphosphino )-2,6-diaminopyridine with MII and M0 transition metals [MII=nickel, palladium, platinum; MO=chromium, molybdenum, tungsten]", Zeitschriftfuer Anorganische und Allgemeine Chemie 545, 1987, 83-97.
Schirmer, et al., "Preparation, properties, and molecular structures of a rigid tridentate chelate ligand N,N'-bis(diphenylphosphino)-2,6-diaminopyridine with MII and M0 transition metals, etc", N Database CA[Online] chemical Abstracts Service, Columbus, Ohio, US, 1987, 83-97.
Song, et al., "N-Heterocyclic Carbene Catalyzed Trifluoromethylation of Carbonyl Compounds", American Chemical Society, 2005, 2193-2196.
Tao, et al., "Ruthenium(II) pincer complexes with oxazoline arms for efficient transfer hydrogenation reactions", Tetrahedron Letters 53, 2012, 4409-4412.
Taylor, et al., "Amidines, isothioureas, and guanidines as nucleophilic catalysts", Chem. Soc. Rev., 2012, 2109-2121.
Trincado, et al., "Cooperating Ligands in Catalysis", 2015, 67-110.
Li, et al., "A Pseudodearomatized PN3P*Ni—H Complex as a Ligand and σ-Nucleophilic Catalyst", J. Org. Chem. 2018, 83, 14969-14977.

* cited by examiner

Complex 3 of Scheme 6

Complex 4 of Scheme 6

IMINES WITH TUNABLE NUCLEOPHILICITY AND STERIC PROPERTIES THROUGH METAL COORDINATION: APPLICATIONS AS LIGANDS AND METALLOORGANOCATALYSTS

CROSS REFERENCE TO RELATED APPLICATIONS

This International Application claims priority to U.S. Provisional Patent Application Ser. No. 62/049,022, filed Sep. 11, 2014, entitled "Novel Imines with tunable nucleophilicity and steric properties through metal coordination: Applications as ligands and Metalloorganocatalysts", the contents of which are incorporated herein in their entirety for all purposes.

FIELD OF THE INVENTION

The present invention relates generally to the field of chemistry and catalysis. More particularly, it relates to phospho-amino pincer-type ligands, metal complexes thereof, and catalytic methods comprising such metal complexes.

BACKGROUND OF THE INVENTION

Applications of molecular organometallic/coordination complexes as catalysts in organic transformations have been studied, and these reactions typically proceed at the metal atom as the catalytic center whose activity and selectivity are manipulated by modifying the steric and/or electronic properties of the surrounding organic ligands.[1,2] On the other hand, organocatalysts are small organic molecules containing no metal atoms that accelerate chemical reactions typically via nucleophilic covalent- or hydrogen bonding activations, and their activity and selectivity can also be tuned by varying the steric and/or electronic factors of the substituent groups.[3-7] Since the coordination to a metal center could influence the property of the ligand, it is conceivable that this interaction could in principle be utilized to offer new strategies for the design and modifications of "organocatalysts" through changing the coordinated metal and its spectator ligands. Such an idea, however, has not been comprehensively examined, presumably due to the highly reactive nature of the metal atoms. Nevertheless, the possibility of enhancing the reactivity of the ligand through complexation with a metal is desired. For example, "cooperating" ligands can participate directly in the bond breaking and forming step together with the metal center to activate substrates to achieve metal-ligand cooperative catalysis.[8-13]

Therefore, a need exists for the development of novel catalyst systems that overcome one or more of the current disadvantages noted above or expand upon what is currently known.

BRIEF SUMMARY OF THE INVENTION

In one aspect, $PN^3$-pincer ligands are provided, with corresponding intermediates, and metal complexes thereof. These $PN^3$-pincer complexes have been found to convert carbon dioxide into methanol.

In one embodiment, a complex is presented that includes a ligand and a metal or metal ion, M, wherein the ligand is a compound according to formula (I), or a deprotonated version thereof, and the ligand is associated with the metal or metal ion, M,

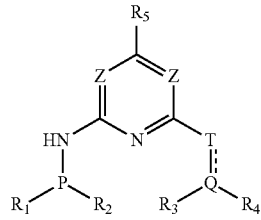

(I)

wherein $R_1$ and $R_2$, are each independently alkyl$_{(C\leq12)}$, aryl$_{(C\leq12)}$, aralkyl$_{(C\leq12)}$, or a substituted version of any of these groups;

$R_3$, and $R_4$, if present, are each independently alkyl$_{(C\leq12)}$, aryl$_{(C\leq12)}$, aralkyl$_{(C\leq12)}$, or a substituted version of any of these groups;

$R_5$ is a hydrogen atom or an alkyl$_{(C\leq12)}$, aryl$_{(C\leq12)}$, aralkyl$_{(C\leq12)}$, amino, hydroxyl, alkoxyl or a substituted version of any of these groups;

each Z, independently, is $CR_6$, N or P;

$R_6$ is a hydrogen atom or an alkyl$_{(C\leq12)}$, aryl$_{(C\leq12)}$, aralkyl$_{(C\leq12)}$, amino, hydroxyl, alkoxyl or a substituted version of any of these groups;

T is a N, $NR_7$, $CR_8$, or $CR_9R_{10}$;

$R_7$, $R_8$, $R_9$ and $R_{10}$ are each independently a hydrogen, alkyl$_{(C\leq12)}$, aryl$_{(C\leq12)}$, aralkyl$_{(C\leq12)}$, or a substituted version of any of these groups;

Q is P or N;

optionally, wherein T and Q, together, form a 5 or 6 membered heterocyclic ring; wherein the heterocyclic ring can optionally be substituted with one or more heteroatoms and or one or more sites of the heterocyclic ring are substituted with one or more alkyl$_{(C\leq12)}$, aryl$_{(C\leq12)}$, aralkyl$_{(C\leq12)}$, or a substituted version of any of these groups, and optionally wherein the heterocyclic ring can have a fused ring attached thereto, provided when T and Q form a 5 or 6 membered heterocyclic ring, $R_3$ and $R_4$ are not present;

====== designates a single bond or a double bond;

M is nickel (Ni) or a nickel ion or salt; and

X is a halide or a hydrogen atom associated with M or the complex.

In another embodiment, a compound of formula (II) is provided as:

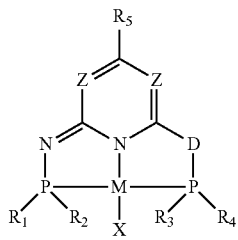

(II)

wherein $R_1$, $R_2$, $R_3$, and $R_4$ are each independently alkyl$_{(C\leq12)}$, aryl$_{(C\leq12)}$, aralkyl$_{(C\leq12)}$, or a substituted version of any of these groups;

$R_5$ is a hydrogen atom or an alkyl$_{(C\leq12)}$, aryl$_{(C\leq12)}$, aralkyl$_{(C\leq12)}$, or a substituted version of any of these groups;

each Z, independently, is $CR_6$, N or P;

$R_6$ is a hydrogen atom or an $alkyl_{(C\leq 12)}$, $aryl_{(C\leq 12)}$, $aralkyl_{(C\leq 12)}$, amino, hydroxyl, alkoxyl or a substituted version of any of these groups;

D is $NR_7$ or $CR_9R_{10}$;

$R_7$, $R_9$ and $R_{10}$ are each independently a hydrogen, $alkyl_{(C\leq 12)}$, $aryl_{(C\leq 12)}$, $aralkyl_{(C\leq 12)}$, or a substituted version of any of these groups;

M is a nickel (Ni) or a nickel ion or salt; and

X is a halide or a hydrogen atom.

In one aspect, D is $NR_7$.

In still another embodiment, a composition of formula (III) is provided as:

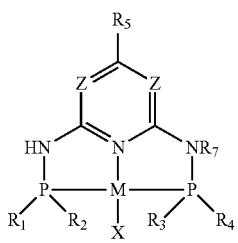

(III)

wherein $R_1$, $R_2$, $R_3$, and $R_4$ are each independently $alkyl_{(C\leq 12)}$, $aryl_{(C\leq 12)}$, $aralkyl_{(C\leq 12)}$, or a substituted version of any of these groups;

$R_5$ is a hydrogen atom or an $alkyl_{(C\leq 12)}$, $aryl_{(C\leq 12)}$, $aralkyl_{(C\leq 12)}$, or a substituted version of any of these groups;

each Z, independently, is $CR_6$, N or P;

$R_6$ is a hydrogen atom or an $alkyl_{(C\leq 12)}$, $aryl_{(C\leq 12)}$, $aralkyl_{(C\leq 12)}$, amino, hydroxyl, alkoxyl or a substituted version of any of these groups;

$R_7$ is a hydrogen, $alkyl_{(C\leq 12)}$, $aryl_{(C\leq 12)}$, $aralkyl_{(C\leq 12)}$, or a substituted version of any of these groups;

M is nickel (Ni), a nickel ion or nickel salt;

X is a halide or a hydrogen atom; and a base.

In one aspect for the various embodiments, $R_1$, $R_2$, $R_3$, and $R_4$ are each an $alkyl_{(C2-10)}$, each Z is CH, T, if present, is N or $NR_7$ and $R_5$ is a hydrogen atom.

In another aspect for the various embodiments, $R_1$, $R_2$, $R_3$, and $R_4$ are each a $C_4$ alkyl and T, if present, is $NR_7$, wherein $R_7$ is a methyl group or a hydrogen atom (hydride).

In still yet another aspect for the various embodiments, X is a hydrogen atom (a hydride).

In yet another aspect for the various embodiments, X is a halide.

In one aspect, the present disclosure provides phospho-amino ligands and methods which include the use of the ligands and their complexes described herein to catalyze reactions between one or more reactants. For example, the phospho-amino ligands described herein, e.g. Formulae (I) through (III), can be used for the conversion of carbon dioxide into methanol, the conversion of aldehydes into alcohols, the conversion of aldehydes in the presence of a trifluoromethylation agent into trifluorinated secondary alcohols, the cycloaddition of carbon dioxide to an epoxide to provide cyclic carbonates and the preparation of an amide from the combination of an alcohol and an amine. These syntheses provide the basis for the useful and unexpected nature of the organocatalysts described herein.

The present embodiments provide advantages such as that the Ni—PN3P complexes have similar reactivities as those of N-heterocyclic carbenes, the production cost is 90% lower than that of carbenes and more specifically, the Ni—PN3P complexes show more efficient reactivity in catalyzing reduction of $CO_2$ to methanol that known complexes.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed descriptions are to be regarded as illustrative in nature and not restrictive.

DETAILED DESCRIPTION

Figure 1:
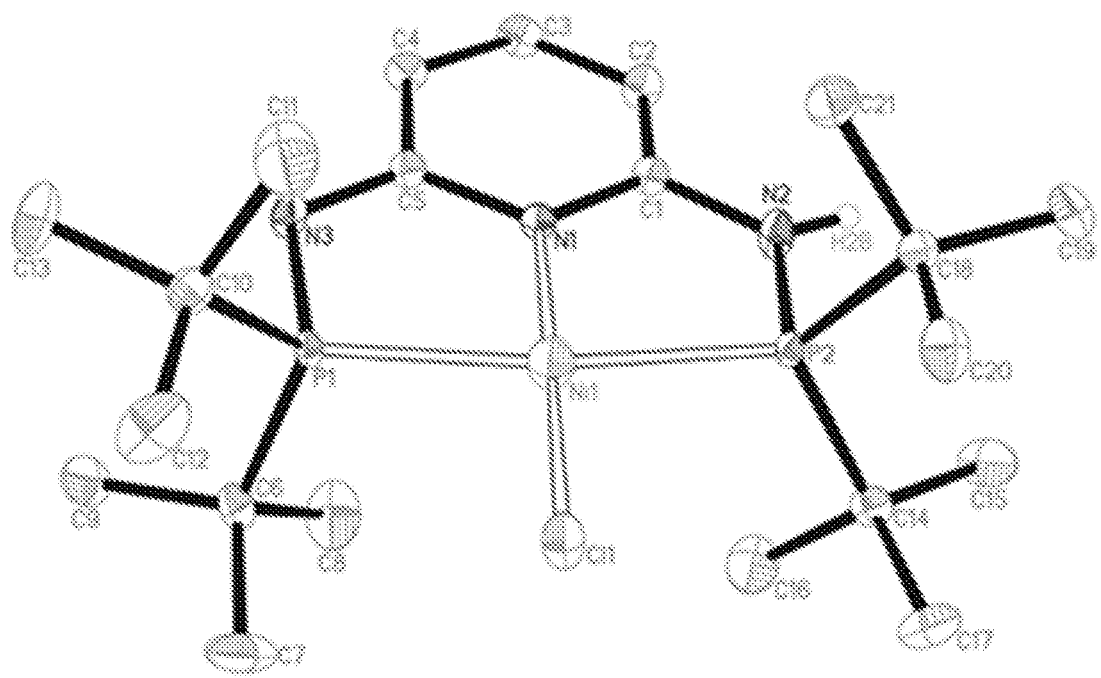
FIG. 1 depicts the molecular structure of complex 1 of Scheme 6. Ni1—N1 1.904, C1—N2 1.392, P2—N2 1.697, C5—N3 1.322, P1—N3 1.661, Ni1—Cl1 2.188, N1—Ni1—Cl1 178.12.
Figure 2:
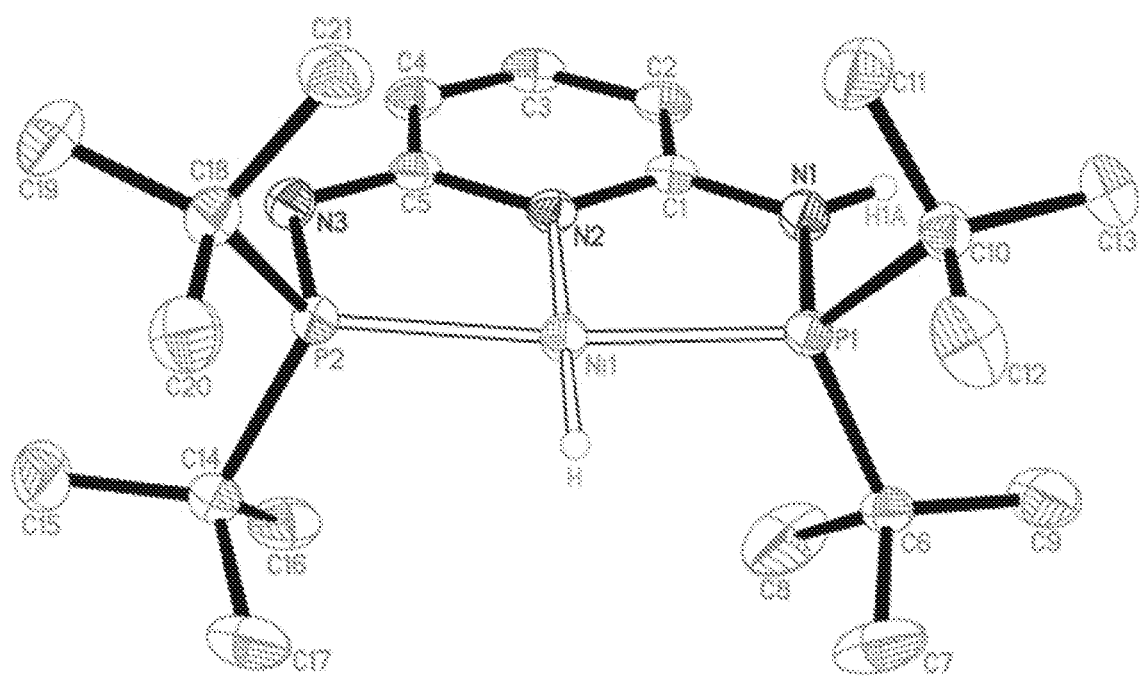
FIG. 2 depicts the molecular structure of complex 2 of Scheme 6. Ni1—N2 1.900, C1—N1 1.380, P1—N1 1.702, C5—N3 1.334, P2—N3 1.673, Ni1—H 1.446, N2—Ni1—H 179.80.

In certain aspects disclosed herein, there are provided a new class of pincer-type ligands, including those having a disubstituted-phosphinoamino (NH—$PR_2$) arm. Metal complexes of such ligands are also provided, including complexes that may be used as catalysts for a variety of transformations, including, for example, conversion of carbon dioxide to methanol.

Upon complexation of ligands described herein to a transition metal and treatment of a base, in some embodiments, the resulting complex can undergo dearomatization after the elimination of H—X.

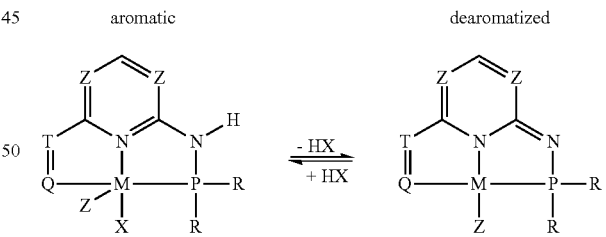

wherein T, Q and Z are as described herein.

A new class of compounds with a general structure shown in Scheme 1a is provided. A series of examples of well-defined nickel $PN^3P$-pincer complexes were prepared (Scheme 1b) and it has been demonstrated that the coordination to the metal center could influence the property of the ligand. Such interactions can be utilized to offer new strategies to design new "metallo-organocatalysts" and ligands. The properties of these compounds can be tuned by modifying the metal center and its spectator ligands, and the substituents in the ligand.

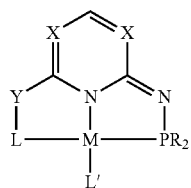

M = transition metal
R = any alkyl or aryl group
X = CH or N
Y — L = doner group such as NH — PR$_2$, CH$_2$PR$_2$, CH$_2$NR$_2$, CH$_2$SR, py, etc
L' = spectator ligands Scheme 1b. Pincer nickel complexes 1-3

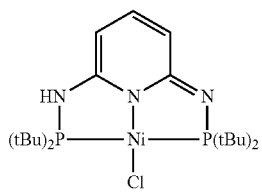

1

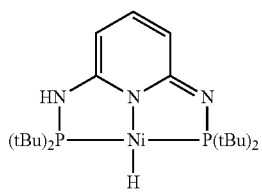

2

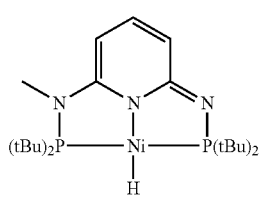

3

The unique reactivities of this new class of imine σ-donor catalysts and ligands have been demonstrated in the following reactions.

Zhang and Ying reported the first N-heterocyclic carbene catalyzed reduction of CO$_2$ with silane under ambient conditions to give methanol with 1840 TON and 25.5 h$^{-1}$ TOF in 2009.[14] Nickel PN$^3$P-pincer complex 2 is an efficient organocatalyst that catalyzed the reduction of CO$_2$ with silane with 4500 TON and 125 h$^{-1}$ TOF, much better than N-heterocyclic carbene (Scheme 2a). It was found that by replacing the chloride ligand to a more σ-donating hydride ligand on the nickel PN$^3$P-pincer complex, the nucleophilicity of the imine N was greatly enhanced to the extent that its reactivity towards carbonyl compounds was higher. The imine N could also activate aldehyde functionality for efficient selective reduction to the corresponding primary alcohols in excellent yields (Scheme 2b).

Scheme 2. Selective conversion of carbon dioxide and aldehydes into alcohols catalyzed by nickel PN$^3$P-pincer complex 2.

(a)

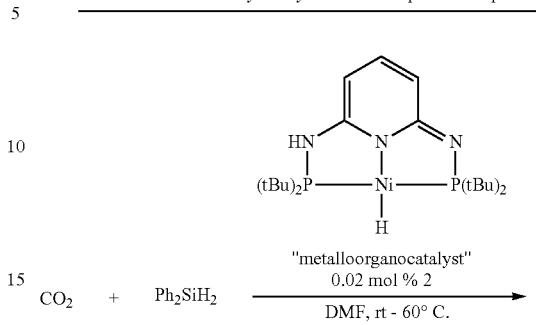

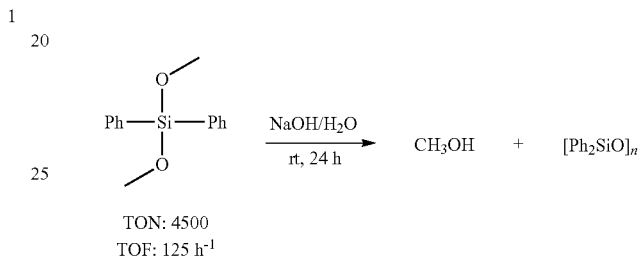

TON: 4500
TOF: 125 h$^{-1}$ (b)

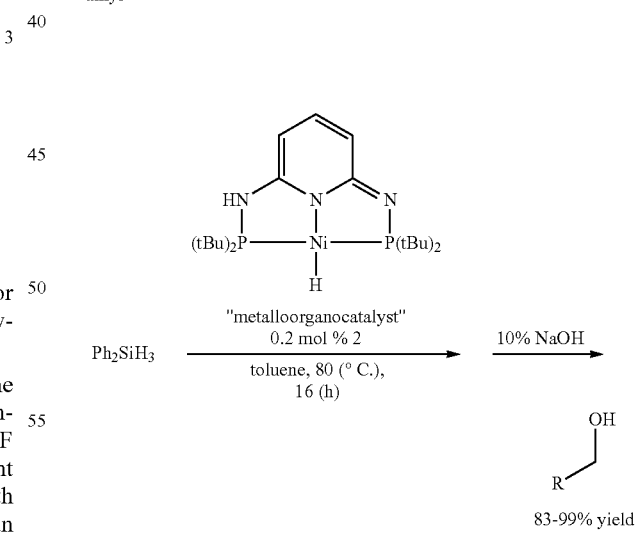

83-99% yield

In 2005, Song and coworkers reported a novel N-heterocyclic carbene catalyzed trifluoromethylation reaction of benzaldehydes.[15] Nickel PN$^3$P-pincer complex 2 served as an organocatalyst like N-heterocyclic carbene to catalyze the trifluoromethylation reaction of benzaldehyde to provide CF$_3$— substituted alcohols in good yield (Scheme 3).

Scheme 3. Trifluoromethylation of Benzaldehyde catalyzed by nickel PN³P-pincer complex 2.

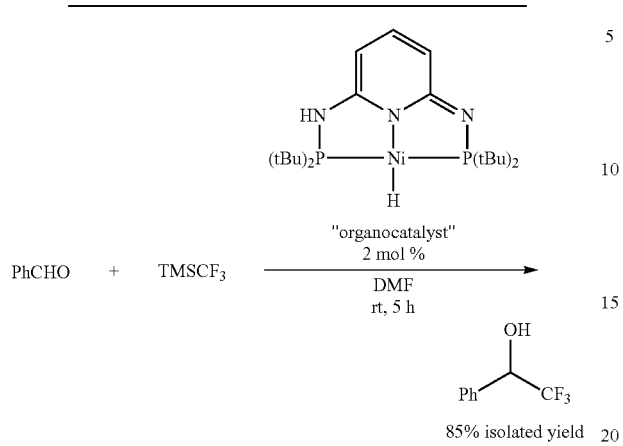

Sartori and coworkers demonstrated that the synthesis of cyclic carbonates by $CO_2$ insertion into epoxides can be carried out under catalytic conditions by using guanidines.[16] Nickel PN³P-pincer complex 2 could also be used as an organocatalyst like guanidine to catalyze the cycloaddition of $CO_2$ to epoxide (Scheme 4).

Scheme 4. Cycloaddition of $CO_2$ to epoxide catalyzed by nickel PN³P-pincer complex 2.

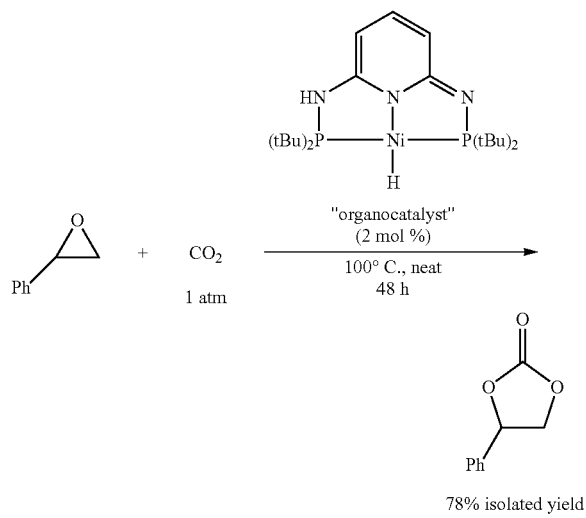

N-heterocyclic carbene based ruthenium complexes were developed as highly active catalysts for the direct amide synthesis from alcohols and amines.[17] Nickel PN³P-pincer complex 2 was used as an efficient ligand like N-heterocyclic carbene for the ruthenium-catalyzed direct amide synthesis from alcohols and amines (Scheme 5).

Scheme 5. Amide synthesis from alcohol and amine catalyzed by nickel PN³P-pincer complex 2 based ruthenium catalyst.

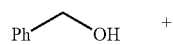

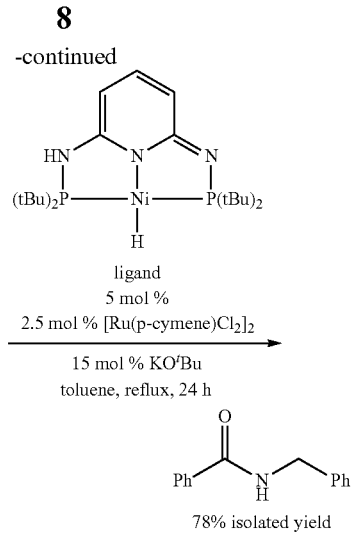

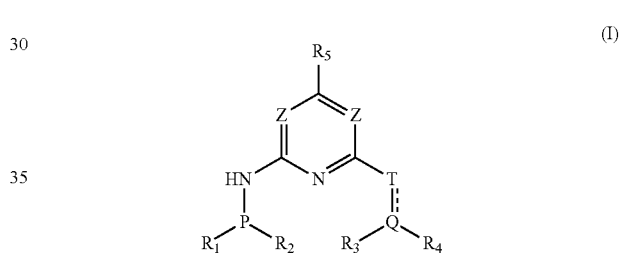

Complexes or compositions disclosed herein can be utilized in the transformations depicted herein. For example, a suitable a ligand and a metal or metal ion, M, wherein the ligand is a compound according to formula (I), or a deprotonated version thereof, and the ligand is associated with the metal or metal ion, M, (I)

wherein $R_1$ and $R_2$, are each independently alkyl$_{(C \leq 12)}$, aryl$_{(C \leq 12)}$, aralkyl$_{(C \leq 12)}$, or a substituted version of any of these groups;

$R_3$, and $R_4$, if present, are each independently alkyl$_{(C \leq 12)}$, aryl$_{(C \leq 12)}$, aralkyl$_{(C \leq 12)}$, or a substituted version of any of these groups;

$R_5$ is a hydrogen atom or an alkyl$_{(C \leq 12)}$, aryl$_{(C \leq 12)}$, aralkyl$_{(C \leq 12)}$, amino, hydroxyl, alkoxyl or a substituted version of any of these groups;

each Z, independently, is $CR_6$, N or P;

$R_6$ is a hydrogen atom or an alkyl$_{(C \leq 12)}$, aryl$_{(C \leq 12)}$, aralkyl$_{(C \leq 12)}$, amino, hydroxyl, alkoxyl or a substituted version of any of these groups;

T is a N, $NR_7$, $CR_8$, or $CR_9R_{10}$;

$R_7$, $R_8$, $R_9$ and $R_{10}$ are each independently a hydrogen, alkyl$_{(C \leq 12)}$, aryl$_{(C \leq 12)}$, aralkyl$_{(C \leq 12)}$, or a substituted version of any of these groups;

Q is P or N;

optionally, wherein T and Q, together, form a 5 or 6 membered heterocyclic ring; wherein the heterocyclic ring can optionally be substituted with one or more heteroatoms and or one or more sites of the heterocyclic ring are substituted with one or more alkyl$_{(C \leq 12)}$, aryl$_{(C \leq 12)}$, aralkyl$_{(C \leq 12)}$, or a substituted version of any of these groups, and optionally wherein the heterocyclic ring can have a fused ring attached thereto, provided when T and Q form a 5 or 6 membered heterocyclic ring, $R_3$ and $R_4$ are not present;

designates a single bond or a double bond;

M is nickel (Ni), a nickel ion or a nickel salt; and

X is a halide or a hydrogen atom associated with M or the complex.

Similarly, complexes or compositions noted herein as formula (II) or (III) can be utilized in the transformations disclosed throughout the specification.

Halides, as noted herein, include, for example, chloride, bromide, iodide, or fluoride.

It should be understood that the dative bonds depicted with metal or metal ion "M" can be covalent, ionic, van der Waals type interactions, complexation interactions or other types of interactions where the metal (M). It should be understood that there is an association with the metal or metal ion and one or more of the nitrogen of the pyridine ring, the dearomatized N of the pyridine ring, a "P", a "T", an NH, an imine nitrogen, or "Q" of the ligands described herein. The stereochemistry of "X" associated with the metal or metal ion "M" is not limited to a planar structure but is merely depicted this way for convenience.

Selected structures include, for example, PN$^3$P-pincer nickel (Ni) complexes 1 through 3, which are useful for dehydrogenation of formic acid are depicted below. Further details regarding different embodiments are provided throughout this disclosure.

Phospho-Amino Pincer-Type Ligands

In one aspect, the disclosure provides compounds of formulae (I) through (III) as well as the ligands for complexes noted throughout.

Examples of such ligands and methods of preparing them, and optionally deprotonating them, are provided throughout this disclosure. For example, see He, L.-P.; Chen, T.; Gong, D.; Lai, Z.-P.; Huang, K.-W. *Organometallics* 2012, 31, 5208-5211. C2. Chen, T.; He, L.; Gong, D.; Yang, L.; Maio, X.; Eppinger, J.; Huang, K.-W. *Tetrahedron Lett.* 2012, 53, 4409-4412. C3. He, L.-P.; Chen, T.; Xue, D.; Eddaoudi, M.; Huang, K.-W. *J. Organomet. Chem.* 2012, 700, 202-206, the contents of which are incorporated herein in their entirety.

These methods can be further modified and optimized using the principles and techniques of organic chemistry as applied by a person skilled in the art. Such principles and techniques are taught, for example, in March's Advanced Organic Chemistry: Reactions, Mechanisms, and Structure (2007), which is incorporated by reference herein. The above methods can be further modified and optimized for preparative, pilot- or large-scale production, either batch of continuous, using the principles and techniques of process chemistry as applied by a person skilled in the art. Such principles and techniques are taught, for example, in Practical Process Research & Development (2000), which is incorporated by reference herein.

Phospho-Amino, Pincer-Type Ligand Complexes and Methods of Use

The present disclosure also provides metal complexes of this novel class of ligands. Such complexes may be used to facilitate a variety of organic transformations, including conversion of carbon dioxide to methanol, conversion of aldehydes into alcohols, conversion of aldehydes in the presence of a trifluoromethylation agent into trifluorinated secondary alcohols, cycloaddition of carbon dioxide to an epoxide to provide cyclic carbonates and preparation of an amide from the combination of an alcohol and an amine.

For example, nickel complexes of ligands can be made, and optionally deprotonated, to provide a dearomatized pyridine moiety and an imine arm. Nickel complexes of ligands 1, 2 and 3 can catalyze, for example, the conversion of aldehydes to alcohols (Tables 1 and 2) or carbon dioxide to methanol (Table 3).

The above methods can be further modified and optimized for preparative, pilot- or large-scale production, either batch of continuous, using the principles and techniques of process chemistry as applied by a person skilled in the art. Such principles and techniques are taught, for example, in Practical Process Research & Development (2000), which is incorporated by reference herein.

Definitions

When used in the context of a chemical group, "hydrogen" means —H; "hydroxy" means —OH; "oxo" means =O; "halo" means independently —F, —Cl, —Br or —I; "amino" means —NH$_2$ (see below for definitions of groups containing the term amino, e.g., alkylamino); "hydroxyamino" means —NHOH; "nitro" means —NO$_2$; imino means =NH (see below for definitions of groups containing the term imino, e.g., alkylimino); "cyano" means —CN; "isocyanate" means —N=C=O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; "thio" means =S; "thioether" means —S—; "sulfonamido" means —NHS(O)$_2$— (see below for definitions of groups containing the term sulfonamido, e.g., alkylsulfonamido); "sulfonyl" means —S(O)$_2$— (see below for definitions of groups containing the term sulfonyl, e.g., alkylsulfonyl); and "sulfinyl" means —S(O)— (see below for definitions of groups containing the term sulfinyl, e.g., alkylsulfinyl).

In the context of chemical formulas, the symbol "—" means a single bond, "=" means a double bond, and "≡" means triple bond. The symbol "----" represents an optional bond, which if present is either single or double. The symbol " ▭▭▭▭ " represents a single bond or a double bond. Thus, for example, the structure

includes the structures

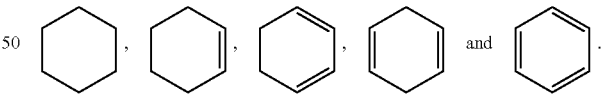

As will be understood by a person of skill in the art, no one such ring atom forms part of more than one double bond. The symbol " ⌒ ", when drawn perpendicularly across a bond indicates a point of attachment of the group. It is noted that the point of attachment is typically only identified in this manner for larger groups in order to assist the reader in rapidly and unambiguously identifying a point of attachment. The symbol " ◂▬ " means a single bond where the group attached to the thick end of the wedge is "out of the page." The symbol " ▬▬▬ " means a single bond where the group attached to the thick end of the wedge is "into the page". The symbol " ⌒ " means a single bond where the conformation (e.g., either R or S) or the geometry is undefined (e.g., either E or Z).

Any undefined valency on an atom of a structure shown in this application implicitly represents a hydrogen atom bonded to the atom. When a group "R" is depicted as a "floating group" on a ring system, for example, in the formula:

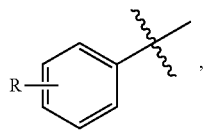

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

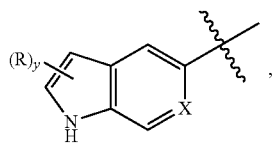

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the groups and classes below, the following parenthetical subscripts further define the group/class as follows: "(Cn)" defines the exact number (n) of carbon atoms in the group/class. "(C≤n)" defines the maximum number (n) of carbon atoms that can be in the group/class, with the minimum number as small as possible for the group in question, e.g., it is understood that the minimum number of carbon atoms in the group "alkenyl$_{(C≤8)}$" or the class "alkene$_{(C≤8)}$" is two. For example, "alkoxy$_{(C≤10)}$" designates those alkoxy groups having from 1 to 10 carbon atoms (e.g., 1, 2, 3, 4, 5, 6, 7, 8, 9, or 10, or any range derivable therein (e.g., 3 to 10 carbon atoms). (Cn-n') defines both the minimum (n) and maximum number (n') of carbon atoms in the group. Similarly, "alkyl$_{(C2-10)}$" designates those alkyl groups having from 2 to 10 carbon atoms (e.g., 2, 3, 4, 5, 6, 7, 8, 9, or 10, or any range derivable therein (e.g., 3 to 10 carbon atoms)).

The term "saturated" as used herein means the compound or group so modified has no carbon-carbon double and no carbon-carbon triple bonds, except as noted below. The term does not preclude carbon-heteroatom multiple bonds, for example a carbon oxygen double bond or a carbon nitrogen double bond. Moreover, it does not preclude a carbon-carbon double bond that may occur as part of keto-enol tautomerism or imine/enamine tautomerism.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single bonds (alkanes/alkyl), or unsaturated, with one or more double bonds (alkenes/alkenyl) or with one or more triple bonds (alkynes/alkynyl). When the term "aliphatic" is used without the "substituted" modifier only carbon and hydrogen atoms are present. When the term is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$ or —OC(O)CH$_3$.

The term "alkyl" when used without the "substituted" modifier refers to a monovalent saturated aliphatic group with a carbon atom as the point of attachment, a linear or branched, cyclo, cyclic or acyclic structure, and no atoms other than carbon and hydrogen. Thus, as used herein cycloalkyl is a subset of alkyl. The groups —CH$_3$ (Me), —CH$_2$CH$_3$ (Et), —CH$_2$CH$_2$CH$_3$ (n-Pr), —CH(CH$_3$)$_2$ (iso-Pr), —CH(CH$_2$)$_2$ (cyclopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (iso-butyl), —C(CH$_3$)$_3$ (tert-butyl), —CH$_2$C(CH$_3$)$_3$ (neopentyl), cyclobutyl, cyclopentyl, cyclohexyl, and cyclohexylmethyl are non-limiting examples of alkyl groups. The term "alkanediyl" when used without the "substituted" modifier refers to a divalent saturated aliphatic group, with one or two saturated carbon atom(s) as the point(s) of attachment, a linear or branched, cyclo, cyclic or acyclic structure, no carbon-carbon double or triple bonds, and no atoms other than carbon and hydrogen. The groups, —CH$_2$— (methylene), —CH$_2$CH$_2$—, —CH$_2$C(CH$_3$)$_2$CH$_2$—, —CH$_2$CH$_2$CH$_2$—, and

are non-limiting examples of alkanediyl groups. The term "alkylidene" when used without the "substituted" modifier refers to the divalent group =CRR' in which R and R' are independently hydrogen, alkyl, or R and R' are taken together to represent an alkanediyl having at least two carbon atoms. Non-limiting examples of alkylidene groups include: =CH$_2$, =CH(CH$_2$CH$_3$), and =C(CH$_3$)$_2$. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$ or —OC(O)CH$_3$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "fluoroalkyl" is a subset of substituted alkyl, in which one or more hydrogen has been substituted with a fluoro group and no other atoms aside from carbon, hydrogen and fluorine are present. The groups, —CH₂F, —CF₃, and —CH₂CF₃ are non-limiting examples of fluoroalkyl groups. An "alkane" refers to the compound H—R, wherein R is alkyl.

The term "alkenyl" when used without the "substituted" modifier refers to an monovalent unsaturated aliphatic group with a carbon atom as the point of attachment, a linear or branched, cyclo, cyclic or acyclic structure, at least one nonaromatic carbon-carbon double bond, no carbon-carbon triple bonds, and no atoms other than carbon and hydrogen. Non-limiting examples of alkenyl groups include: —CH=CH₂ (vinyl), —CH=CHCH₃, —CH=CHCH₂CH₃, —CH₂CH=CH₂ (allyl), —CH₂CH=CHCH₃, and —CH=CH—C₆H₅. The term "alkenediyl" when used without the "substituted" modifier refers to a divalent unsaturated aliphatic group, with two carbon atoms as points of attachment, a linear or branched, cyclo, cyclic or acyclic structure, at least one nonaromatic carbon-carbon double bond, no carbon-carbon triple bonds, and no atoms other than carbon and hydrogen. The groups, —CH=CH—, —CH=C(CH₃)CH₂—, —CH=CHCH₂—, and

are non-limiting examples of alkenediyl groups. When these terms are used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —N(CH₃)₂, —C(O)NH₂ or —OC(O)CH₃. The groups, —CH=CHF, —CH=CHCl and —CH=CHBr, are non-limiting examples of substituted alkenyl groups. An "alkene" refers to the compound H—R, wherein R is alkenyl.

The term "alkynyl" when used without the "substituted" modifier refers to an monovalent unsaturated aliphatic group with a carbon atom as the point of attachment, a linear or branched, cyclo, cyclic or acyclic structure, at least one carbon-carbon triple bond, and no atoms other than carbon and hydrogen. As used herein, the term alkynyl does not preclude the presence of one or more non-aromatic carbon-carbon double bonds. The groups, —C≡CH, —C≡CCH₃, and —CH₂C≡CCH₃, are non-limiting examples of alkynyl groups. The term "alkynediyl" when used without the "substituted" modifier refers to a divalent unsaturated aliphatic group, with two carbon atoms as points of attachment, a linear or branched, cyclo, cyclic or acyclic structure, at least one carbon-carbon triple bond, and no atoms other than carbon and hydrogen. When these terms are used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —N(CH₃)₂, —C(O) NH₂ or —OC(O)CH₃. An "alkyne" refers to the compound H—R, wherein R is alkynyl.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or not fused. As used herein, the term does not preclude the presence of one or more alkyl group (carbon number limitation permitting) attached to the first aromatic ring or any additional aromatic ring present. Non-limiting examples of aryl groups include phenyl (Ph), methylphenyl, (dimethyl)phenyl, —C₆H₄CH₂CH₃ (ethylphenyl), naphthyl, and the monovalent group derived from biphenyl. The term "arenediyl" when used without the "substituted" modifier refers to a divalent aromatic group, with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl group (carbon number limitation permitting) attached to the first aromatic ring or any additional aromatic ring present. If more than one ring is present, the rings may be fused or unfused. Non-limiting examples of arenediyl groups include:

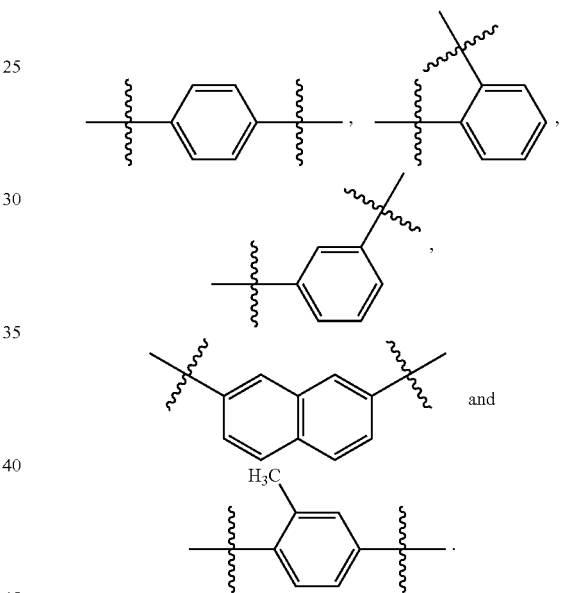

When these terms are used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O) CH₃, —N(CH₃)₂, —C(O)NH₂ or —OC(O)CH₃. An "arene" refers to the compound H—R, wherein R is aryl.

The term "aralkyl" when used without the "substituted" modifier refers to the monovalent group -alkanediyl-aryl, in which the terms alkanediyl and aryl are each used in a manner consistent with the definitions provided above. Non-limiting examples of aralkyls are: phenylmethyl (benzyl, Bn) and 2-phenyl-ethyl. When the term is used with the "substituted" modifier one or more hydrogen atom from the alkanediyl and/or the aryl has been independently replaced by —OH, —F, —Cl, —Br, —I, —NH₂, —NO₂, —CO₂H, —CO₂CH₃, —CN, —SH, —OCH₃, —OCH₂CH₃, —C(O) CH₃, —N(CH₃)₂, —C(O)NH₂ or —OC(O)CH₃. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of an aromatic ring structure wherein at least one of the ring atoms is nitrogen, oxygen or sulfur, and wherein the group consists of no atoms other than carbon, hydrogen, aromatic nitrogen, aromatic oxygen and aromatic sulfur. As used herein, the term does not preclude the presence of one or more alkyl group (carbon number limitation permitting) attached to the aromatic ring or any additional aromatic ring present. Non-limiting examples of heteroaryl groups include furanyl, imidazolyl, indolyl, indazolyl (Im), methylpyridyl, oxazolyl, pyridyl, pyrrolyl, pyrimidyl, pyrazinyl, quinolyl, quinazolyl, quinoxalinyl, thienyl, and triazinyl. The term "heteroarenediyl" when used without the "substituted" modifier refers to an divalent aromatic group, with two aromatic carbon atoms, two aromatic nitrogen atoms, or one aromatic carbon atom and one aromatic nitrogen atom as the two points of attachment, said atoms forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. As used herein, the term does not preclude the presence of one or more alkyl group (carbon number limitation permitting) attached to the first aromatic ring or any additional aromatic ring present. If more than one ring is present, the rings may be fused or unfused. Non-limiting examples of heteroarenediyl groups include:

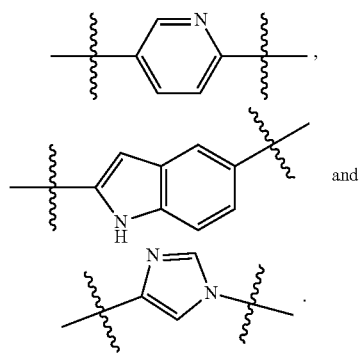

and

When these terms are used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —N(CH₃)₂, —C(O)NH₂ or —OC(O)CH₃.

The term "acyl" when used without the "substituted" modifier refers to the group —C(O)R, in which R is a hydrogen, alkyl, aryl, aralkyl or heteroaryl, as those terms are defined above. The groups, —CHO, —C(O)CH₃ (acetyl, Ac), —C(O)CH₂CH₃, —C(O)CH₂CH₂CH₃, —C(O)CH (CH₃)₂, —C(O)CH(CH₂)₂, —C(O)C₆H₅, —C(O)C₆H₄CH₃, —C(O)CH₂C₆H₅, —C(O)(imidazolyl) are non-limiting examples of acyl groups. A "thioacyl" is defined in an analogous manner, except that the oxygen atom of the group —C(O)R has been replaced with a sulfur atom, —C(S)R. When either of these terms are used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —N(CH₃)₂, —C(O)NH₂ or —OC(O)CH₃. The groups, —C(O)CH₂CF₃, —CO₂H (carboxyl), —CO₂CH₃ (methylcarboxyl), —CO₂CH₂CH₃, —C(O)NH₂ (carbamoyl), and —CON(CH₃)₂, are non-limiting examples of substituted acyl groups.

The term "alkoxy" when used without the "substituted" modifier refers to the group —OR, in which R is an alkyl, as that term is defined above. Non-limiting examples of alkoxy groups include: —OCH₃, —OCH₂CH₃, —OCH₂CH₂CH₃, —OCH(CH₃)₂, —OCH(CH₂)₂, —O-cyclopentyl, and —O-cyclohexyl. The terms "alkenyloxy", "alkynyloxy", "aryloxy", "aralkoxy", "heteroaryloxy", and "acyloxy", when used without the "substituted" modifier, refers to groups, defined as —OR, in which R is alkenyl, alkynyl, aryl, aralkyl, heteroaryl, and acyl, respectively. Similarly, the term "alkylthio" when used without the "substituted" modifier refers to the group —SR, in which R is an alkyl, as that term is defined above. When any of these terms is used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —N(CH₃)₂, —C(O)NH₂ or —OC(O)CH₃. The term "alcohol" corresponds to an alkane, as defined above, wherein at least one of the hydrogen atoms has been replaced with a hydroxy group.

The term "alkylamino" when used without the "substituted" modifier refers to the group —NHR, in which R is an alkyl, as that term is defined above. Non-limiting examples of alkylamino groups include: —NHCH₃ and —NHCH₂CH₃. The term "dialkylamino" when used without the "substituted" modifier refers to the group —NRR', in which R and R' can be the same or different alkyl groups, or R and R' can be taken together to represent an alkanediyl. Non-limiting examples of dialkylamino groups include: —N(CH₃)₂, —N(CH₃)(CH₂CH₃), and N-pyrrolidinyl. The terms "alkoxyamino", "alkenylamino", "alkynylamino", "arylamino", "aralkylamino", "heteroarylamino", and "alkylsulfonylamino" when used without the "substituted" modifier, refers to groups, defined as —NHR, in which R is alkoxy, alkenyl, alkynyl, aryl, aralkyl, heteroaryl, and alkylsulfonyl, respectively. A non-limiting example of an arylamino group is —NHC₆H₅. The term "amido" (acylamino), when used without the "substituted" modifier, refers to the group —NHR, in which R is acyl, as that term is defined above. A non-limiting example of an amido group is —NHC(O)CH₃. The term "alkylimino" when used without the "substituted" modifier refers to the divalent group =NR, in which R is an alkyl, as that term is defined above. When any of these terms is used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —N(CH₃)₂, —C(O)NH₂ or —OC(O)CH₃. The groups —NHC(O)OCH₃ and —NHC(O)NHCH₃ are non-limiting examples of substituted amido groups.

The above definitions supersede any conflicting definition in any of the reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

In the specification and in the claims, the terms "including" and "comprising" are open-ended terms and should be interpreted to mean "including, but not limited to . . . " These terms encompass the more restrictive terms "consisting essentially of" and "consisting of."

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

The following paragraphs enumerated consecutively from 1 through 30 provide for various aspects of the embodiments described herein. In one embodiment, in a first paragraph (1), the present invention provides a complex comprising a ligand and a metal or metal ion, M, wherein the ligand is a compound according to formula (I), or a deprotonated version thereof, and the ligand is associated with the metal or metal ion, M,

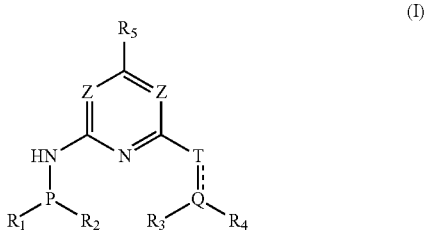

(I)

wherein $R_1$ and $R_2$, are each independently alkyl$_{(C\leq12)}$, aryl$_{(C\leq12)}$, aralkyl$_{(C\leq12)}$, or a substituted version of any of these groups;

$R_3$, and $R_4$, if present, are each independently alkyl$_{(C\leq12)}$, aryl$_{(C\leq12)}$, aralkyl$_{(C\leq12)}$, or a substituted version of any of these groups;

$R_5$ is a hydrogen atom or an alkyl$_{(C\leq12)}$, aryl$_{(C\leq12)}$, aralkyl$_{(C\leq12)}$, amino, hydroxyl, alkoxyl or a substituted version of any of these groups;

each Z, independently, is $CR_6$, N or P;

$R_6$ is a hydrogen atom or an alkyl$_{(C\leq12)}$, aryl$_{(C\leq12)}$, aralkyl$_{(C\leq12)}$, amino, hydroxyl, alkoxyl or a substituted version of any of these groups;

T is a N, $NR_7$, $CR_8$, or $CR_9R_{10}$;

$R_7$, $R_8$, $R_9$ and $R_{10}$ are each independently a hydrogen, alkyl$_{(C\leq12)}$, aryl$_{(C\leq12)}$, aralkyl$_{(C\leq12)}$, or a substituted version of any of these groups;

Q is P or N;

optionally, wherein T and Q, together, form a 5 or 6 membered heterocyclic ring; wherein the heterocyclic ring can optionally be substituted with one or more heteroatoms and or one or more sites of the heterocyclic ring are substituted with one or more alkyl$_{(C\leq12)}$, aryl$_{(C\leq12)}$, aralkyl$_{(C\leq12)}$, or a substituted version of any of these groups, and optionally wherein the heterocyclic ring can have a fused ring attached thereto, provided when T and Q form a 5 or 6 membered heterocyclic ring, $R_3$ and $R_4$ are not present;

------ designates a single bond or a double bond;

M is nickel (Ni), a nickel ion or a nickel salt; and

X is a halide or a hydrogen atom associated with M or the complex.

2. The composition of paragraph 1, wherein $R_1$, $R_2$, $R_3$, and $R_4$ are each a alkyl$_{(C2-10)}$, each Z is CH, T is N or $NR_7$ and $R_5$ is a hydrogen atom.

3. The composition of paragraph 2, wherein $R_1$, $R_2$, $R_3$, and $R_4$ are each a $C_4$ alkyl and T is $NR_7$.

4. The composition of any of paragraphs 1 through 3, wherein $R_7$ is a methyl group or a hydrogen.

5. The composition of any of paragraphs 1 through 4, wherein X is a hydrogen atom (a hydride).

6. The compound of any of paragraphs 1 through 4, wherein X is a halide.

7. A compound comprising formula (II):

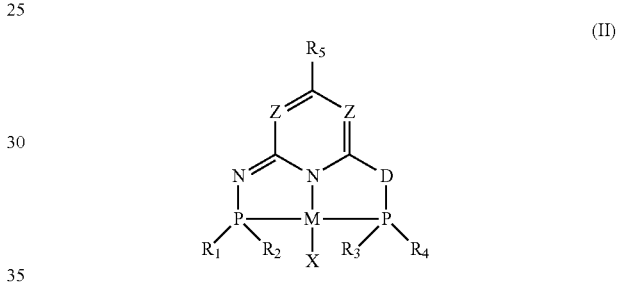

(II)

wherein $R_1$, $R_2$, $R_3$, and $R_4$ are each independently alkyl$_{(C\leq12)}$, aryl$_{(C\leq12)}$, aralkyl$_{(C\leq12)}$, or a substituted version of any of these groups;

$R_5$ is a hydrogen atom or an alkyl$_{(C\leq12)}$, aryl$_{(C\leq12)}$, aralkyl$_{(C\leq12)}$, or a substituted version of any of these groups;

each Z, independently, is $CR_6$, N or P;

$R_6$ is a hydrogen atom or an alkyl$_{(C\leq12)}$, aryl$_{(C\leq12)}$, aralkyl$_{(C\leq12)}$, amino, hydroxyl, alkoxyl or a substituted version of any of these groups;

D is $NR_7$ or $CR_9R_{10}$; in one aspect, D is $NR_7$.

$R_7$, $R_9$ and $R_{10}$ are each independently a hydrogen, alkyl$_{(C\leq12)}$, aryl$_{(C\leq12)}$, aralkyl$_{(C\leq12)}$, or a substituted version of any of these groups;

M is a nickel (Ni) or a nickel ion or salt; and

X is a halide or a hydrogen atom.

8. The compound of paragraph 7, wherein $R_1$, $R_2$, $R_3$, and $R_4$ are each a alkyl$_{(C2-10)}$, each Z is CH and $R_5$ is a hydrogen atom.

9. The compound of paragraph 8, wherein $R_1$, $R_2$, $R_3$, and $R_4$ are each a $C_4$ alkyl.

10. The compound of any of paragraphs 7 through 9, wherein $R_7$ is a methyl group or a hydrogen.

11. The compound of any of paragraphs 7 through 10, wherein X is a hydrogen atom (a hydride).

12. The compound of any of paragraphs 7 through 10, wherein X is a halide.

13. A composition comprising formula (III):

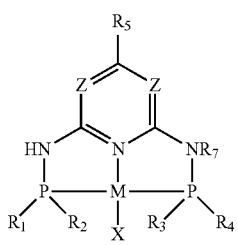

wherein $R_1$, $R_2$, $R_3$, and $R_4$ are each independently alkyl$_{(C≤12)}$, aryl$_{(C≤12)}$, aralkyl$_{(C≤12)}$, or a substituted version of any of these groups;
$R_5$ is a hydrogen atom or an alkyl$_{(C≤12)}$, aryl$_{(C≤12)}$, aralkyl$_{(C≤12)}$, or a substituted version of any of these groups;
each Z, independently, is CR$_6$, N or P;
$R_6$ is a hydrogen atom or an alkyl$_{(C≤12)}$, aryl$_{(C≤12)}$, aralkyl$_{(C≤12)}$, amino, hydroxyl, alkoxyl or a substituted version of any of these groups;
$R_7$ is a hydrogen, alkyl$_{(C≤12)}$, aryl$_{(C≤12)}$, aralkyl$_{(C≤12)}$, or a substituted version of any of these groups;
M is nickel (Ni), a nickel ion or a nickel salt;
X is a halide or a hydrogen atom; and
a base.
14. The composition of paragraph 13, wherein $R_1$, $R_2$, $R_3$, and $R_4$ are each a alkyl$_{(C2-10)}$, each Z is CH and $R_5$ is a hydrogen atom.
15. The composition of paragraph 14, wherein $R_1$, $R_2$, $R_3$, and $R_4$ are each a $C_4$ alkyl.
16. The composition of any of paragraphs 13 through 15, wherein $R_7$ is a methyl group or a hydrogen.
17. The composition of any of paragraphs 13 through 16, wherein X is a hydrogen atom (a hydride).
18. The composition of any of paragraphs 13 through 18, wherein X is a halide.
19. The composition of any of paragraphs 13 through 18, wherein the base is an organic base.
20. The composition of paragraph 19, wherein the organic base is an amine or an alkoxide.
21. The composition of paragraph 20, wherein the amine is an alkylamine comprising NR$_{20}$R$_{21}$R$_{23}$, wherein R$_{20}$, R$_{21}$ and R$_{23}$ are each independently a hydrogen atom, alkyl$_{(C≤12)}$, aryl$_{(C≤12)}$, aralkyl$_{(C≤12)}$, or a substituted version of any of these groups, wherein one or more of R$_{20}$, R$_{21}$ and R$_{22}$ can form a ring or an aromatic amine.
22. The composition of paragraph 21, wherein the aromatic amine is pyridine.
23. A method to prepare methanol from carbon dioxide comprising the step:
contacting carbon dioxide and a silane with the compound or composition of any of paragraphs 1 through 22 to form a mixture, wherein the carbon dioxide is converted to methanol.
24. The method of paragraph 23, wherein the silane is diphenyl silane.
25. The method of either paragraphs 23 or 24, further comprising the step of treating mixture with an aqueous base.
26. A method to prepare alcohols from an aldehyde comprising the step:
contacting an aldehyde and a silane with the compound or composition of any of paragraphs 1 through 22 to form a mixture, wherein the aldehyde is converted to an alcohol.
27. The method of paragraph 26, further comprising the step of treating mixture with an aqueous base.
28. A method to trifluoromethylate an aldehyde comprising the step:
contacting an aldehyde with trifluoromethyltrimethylsilane with the compound or composition of any of paragraphs 1 through 22 to form a mixture, wherein the aldehyde is converted to a trifluoromethyl alcohol product.
29. A method to prepare cyclic carbonates from an alkyl or aryl epoxide and carbon dioxide, comprising the step:
contacting an alkyl or aryl epoxide with carbon dioxide with the compound or composition of any of paragraphs 1 through 22, wherein the alkyl or aryl epoxide is converted into a cyclic carbonate.
30 A method to prepare an amide from an alcohol and an amine comprising the step:
contacting a primary alkyl alcohol or an aryl group containing a primary alcohol and a primary or secondary alkyl or aryl amine with a compound or composition of any of paragraphs 1 through 22 in the presence of a ruthenium catalyst, including ruthenium metal salts, wherein the alcohol and amine are converted into an amide.

EXAMPLES

The most direct synthesis of thee complexes starts with the reaction of the known ligand A and a nickel(II) halide source. Accordingly, complex B was obtained by heating NiCl$_2$ with ligand A in toluene, a similar procedure to that of its bromide analog by Kirchner.[22,23] The following t-BuOK deprotonation afforded the dearomatized pincer nickel complex 1. The preparation of Ni—H complex 2 was achieved by oxidative addition of A to bis(1,5-cyclooctadiene)nickel (0) in toluene (Scheme 6). Upon treatment with t-BuOK and methyl iodide in toluene, complex 2 was methylated to afford pincer Ni—H complex 3.

Scheme 6 Synthesis of nickel complexes 1-3.

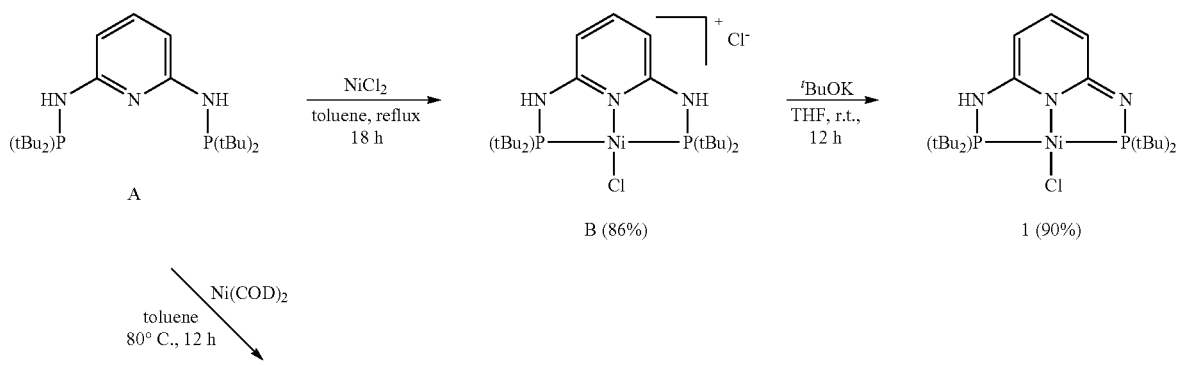

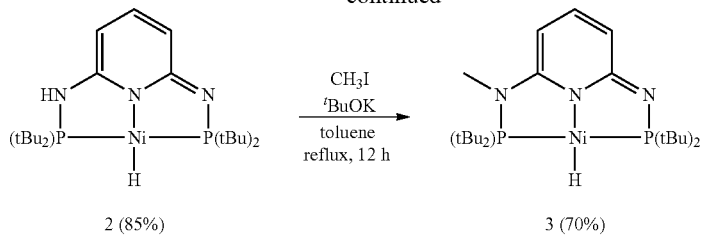

The reaction of benzaldehyde 4a and phenylsilane 5 was investigated in the presence of various pincer nickel complexes (1.0 mol %) and benzyl alcohol was obtained in 99% yield when 2 was employed (Table 1, entry 1). Slightly lower yields of benzyl alcohol were observed when complexes 1 and 3 were tested with longer reaction time (Table 1, entries 2 and 3). No product was observed without using Ni complexes (Table 1, entry 4). These observations suggested that complexes 1-3 serve as the catalyst and 2 was the best among them. Reaction screenings with various solvents (Table 1, entries 5-7), under different temperatures and catalyst loadings (Table 1, entries 8-11) indicated that 0.2 mol % of 2 showed satisfactory catalyst performance in toluene at 80° C.

TABLE 1

Optimization of the reaction conditions in the hydrosilylation of aldehyde 4a catalyzed by nickel PN$^3$P-Pincer Hydride Complexes.[a]

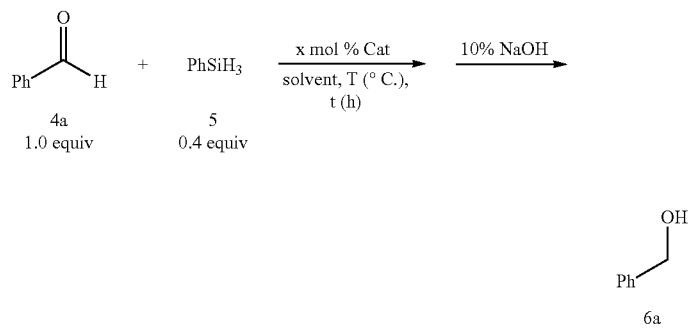

| Entry | Cat. | x | T (° C.) | Solvent | t (h) | yield (%)[b] 6a |
|---|---|---|---|---|---|---|
| 1 | 2 | 1.0 | 80 | toluene | 16 | 99 |
| 2 | 3 | 1.0 | 80 | toluene | 24 | 94 |
| 3 | 1 | 1.0 | 80 | toluene | 48 | 93 |
| 4 | none | — | r.t | toluene | 24 | 0 |
| 5 | 2 | 1.0 | 40 | DCM | 48 | 75 |
| 6 | 2 | 1.0 | 70 | THF | 48 | 83 |
| 7 | 2 | 1.0 | 80 | CH$_3$CN | 48 | 75 |
| 8 | 2 | 1.0 | r.t | toluene | 24 | 10 |
| 9 | 2 | 0.5 | 80 | toluene | 16 | 99 |
| 10 | 2 | 0.2 | 80 | toluene | 16 | 99 |
| 11 | 2 | 0.1 | 80 | toluene | 24 | 88 |

[a]The reaction was carried out on a 0.4-mmol scale, and the ratio of 4a/5 was 1.0/0.4.
[b]Isolated yield after basic work-up.

The scope of this catalytic system was then studied and the reduction products were isolated as alcohols after basic hydrolysis of the resulting silyl ethers. Benzaldehyde 4 bearing either electron-rich or electron-poor functional groups could all react smoothly to give the corresponding alcohols 6 in excellent yields (Table 2). Trans-cinnamaldehyde was converted to cinnamyl alcohol selectively at 60° C. and no sign of 1,4-reduction was detected (Table 2, entry 11), in sharp contrast to the results of similar reactions catalyzed by pincer Ni—H[24] or carbene-Cu—H complexes.[25] Hydrosilylation of a mixture of acetophenone (1.0 equiv.) and benzaldehyde (1.0 equiv.) catalyzed by 2 gave benzyl alcohol 6a in quantitative yield with full recovery of acetophenone, revealing the excellent chemoselectivity towards the aldehyde substrates (Scheme 3).

TABLE 2

Substrate scope of hydrosilylation of aldehyde 4 with 5 catalyzed by 2.[a]

| Entry[a] | R | Isolated yield (%)[b] 6 |
|---|---|---|
| 1 | 4a, X = H | 6a, 99 |
| 2 | 4b, X = 4-Me | 6b, 90 |
| 3 | 4c, X = 3-Me | 6c, 85 |
| 4 | 4d, X = 2-MeO | 6d, 93 |
| 5 | 4e, X = 4-Cl | 6e, 90 |
| 6 | 4f, X = 4-Br | 6f, 96 |
| 7 | 4g, X = 2-CF$_3$ | 6g, 86 |
| 8 | 4h, X = 2-OH | 6h, 91 |
| 9 | 4i, 2-pyridyl | 6i, 94 |
| 10 | 4j, (cyclohexyl-CHO) | 6j, 83 |
| 11 | 4k, (PhCH=CH-CHO) | 6k, 85[c] |

[a]Unless otherwise specified, all reactions were performed on a 1-mmol scale in dry toluene (1 mL) under Ar in the presence of 2 (0.2 mol %) at 80° C.
[b]Isolated yields after basic work-up.
[c]the reaction was performed at 60° C. for 48 h.

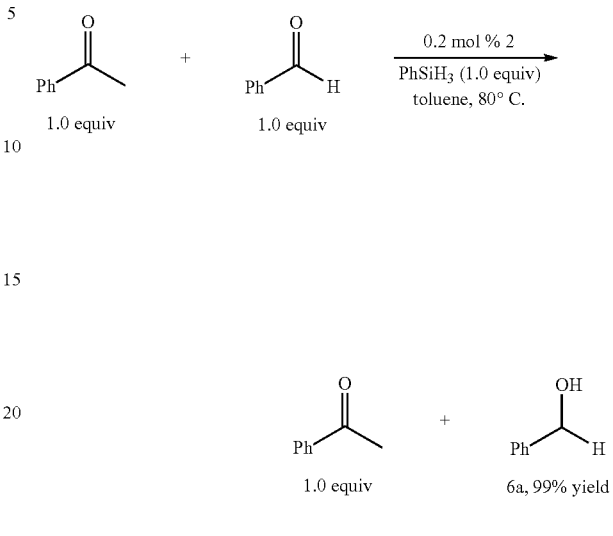

Scheme 8 Hydrosilylation of acetophenone and benzaldehyde catalyzed by 2

Reduction of $CO_2$ was examined with compound 2. It was found that methanol was obtained in 91% yield upon basic hydrolysis workup with 1.25 mol % of 2. This result is similar to that of the hydrosilylation of $CO_2$ catalyzed by N-heterocyclic carbenes reported by Zhang and Ying,[14] but in sharp contrast to those of the reactions catalyzed by metal hydrides, where $CH_4$ was identified as the final product.[26,27] Scheme 9.

Scheme 9 Reduction of $CO_2$ to methanol

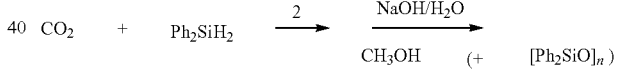

Using tertiary amines, such as $Et_3N$ and DABCO (1,4-Diazabicyclo[2.2.2]octane) and imine, such as DBU (1,8-Diazabicyclo[5.4.0]undec-7-ene) as the catalysts led to no methanol product (Table 3, entries 4-6). The reaction worked well in polar aprotic solvents such as DMF, THF, and MeCN, with slower reaction rates in THF and MeCN (Table 3, entries 7 and 8), presumably because DMF can act as a Lewis base to help to activate silane and thus accelerate the reaction.[28] No reaction was observed in $CH_2Cl_2$ and toluene (Table 3, entries 9 and 10). Further screening of catalyst loadings (Table 3, entries 11-16) revealed that diphenylsilane could be fully consumed with a catalyst loading as low as 0.02 mol % (Table 3, entry 16). The turnover number (TON) and turnover frequency (TOF) for hydride 2 as the catalyst in this reaction could reach 4900 and 136 h$^{-1}$, respectively (Table 3, entry 16), much higher than those of the (N-heterocyclic carbene) NHC catalysts.[14] To the best of our knowledge, this is the highest TON and TOF reported for the reduction of $CO_2$ with silane to methanol.

TABLE 3

The reaction conditions screening for hydrosilyation of $CO_2$ with diphenylsilane catalyzed by nickel $PN^3P$-pincer complexes.[a]

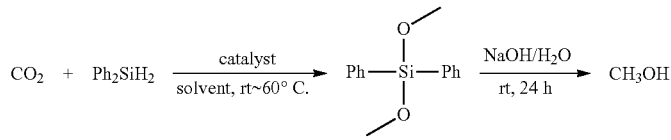 [SMILES: "CO2" ; "Ph2SiH2" ; CO[Si](OC)(c1ccccc1)c1ccccc1 ; "CH3OH"]

| Entry | Catalyst | Catalyst loading [mol % Si—H] | Solvent | t [h][b] | Yield[%][c] |
| --- | --- | --- | --- | --- | --- |
| 1 | 2 | 1.25 | DMF | 12 | 91 |
| 2 | 3 | 1.25 | DMF | 20 | 85 |
| 3 | 1 | 1.25 | DMF | 48 | 88 |
| 4 | Et$_3$N | 1.25 | DMF | 48 | 0 |
| 5 | DABCO | 1.25 | DMF | 48 | 0 |
| 6 | DBU | 1.25 | DMF | 48 | 0 |
| 7 | 2 | 1.25 | THF | 24 | 90 |
| 8 | 2 | 1.25 | MeCN | 36 | 91 |
| 9 | 2 | 1.25 | CH$_2$Cl$_2$ | —[d] | — |
| 10 | 2 | 1.25 | toluene | —[d] | — |
| 11 | 2 | 5.00 | DMF | 6 | 91 |
| 12 | 2 | 2.50 | DMF | 8 | 91 |
| 13 | 2 | 0.50 | DMF | 16 | 92 |
| 14 | 2 | 0.25 | DMF | 24 | 90 |
| 15 | 2 | 0.05 | DMF | 28 | 87 |
| 16 | 2 | 0.02[e] | DMF | 36 | 98 |

[a]Reaction conditions: $CO_2$ balloon, catalyst, 1.0 mmol of diphenylsilane, 1.0 mL of solvent, and the reaction was carried out at rt-60° C.
[b]Time required for the full consumption of diphenylsilane monitored by GC/MS.
[c]Yields of methanol determined by GC.
[d]Nearly no reaction.
[e]2.0 mmol of diphenylsilane was used.

While the conventional wisdom is to modify the reactivities and selectivities of the coordination metal catalysts and organocatalysts through changing the steric and/or electronic properties of organic substituent groups, it is demonstrated herein that the reactivity of the organic imine group could be increased through coordinating to the Ni metal center and changing the spectator ligand on Ni. When the chloride ligand on the Ni center in 1 was replaced with a hydride in 2, the nucleophilicity of the imine N atom was significantly enhanced such that this imine group achieves an improved activity than those of NHCs in nucleophilic covalent bonding activation for the hydrosilylation of carbonyl compounds, the first catalytic activity of its kind for imine groups.

Synthesis of 1: To a suspension of 1,3-(tBu$_2$PNH)$_2$C$_6$H$_4$ (1.0 g, 4.0 mmol) in toluene (20 ml) was added anhydrous NiCl$_2$ (519 mg, 4.0 mmol) under an argon atmosphere, giving an orange suspension. While the solution was being boiled for 18 h, a brown precipitate formed, which was removed by filtration after the mixture was cooled to room temperature. The volume of the orange filtrate was reduced to 5 mL, and then pentane was added to cause precipitation. The product was collected by filtration, washed with pentane (3×3 mL), and dried under vacuum to give an orange powder of complex B (1.96 g, 86% yield). To a THF (5 mL) suspension of B (45 mg, 0.091 mmol) was added tBuOK (11.2 mg, 0.095 mmol), resulting in a color change from yellowish to brown. The solvent was removed under vacuum, and the complex was extracted with benzene. Solvent evaporation yielded complex 1 (40 mg, 90% yield) as an brown solid. IR (neat, cm$^{-1}$): ν=3350 (NH); $^1$H NMR (400 MHz, (CD$_3$)$_2$SO): δ 7.44 (s, 1H), 6.81 (dd, J=8.8, 7.2 Hz, 1H), 5.74 (d, J=8.8, 1H), 5.43 (d, J=7.2 Hz, 1H), 1.38-1.45 (m, 36H); $^{13}$C NMR ((CD$_3$)$_2$SO, 100 MHz): δ 173.1 (d, J=10.3 Hz), 162.6 (dd, J=11.2, 8.6 Hz), 138.6, 101.6 (d, J=21.5 Hz), 88.1 (d, J=7.7 Hz), 38.1 (d, J=5.2 Hz), 37.9 (d, J=5.2 Hz), 37.4 (d, J=2.5 Hz), 37.3 (d, J=2.6 Hz), 27.93, 27.91, 27.65, 27.60; $^{31}$P NMR (162 MHz, (CD$_3$)$_2$SO): δ 59.3 (d, J=285.4 Hz, 1P), 40.1 (d, J=285.4 Hz, 1P); HRMS (ESI) Calcd. for C$_{21}$H$_{41}$ClN$_3$NiP$_2$ requires (M+H$^+$) 490.1818, Found: 490.1796; Elemental analysis (%) for C$_{21}$H$_{40}$ClN$_3$NiP$_2$: Calc. C, 51.41; H, 8.22; N, 8.56. Found: C, 51.59; H, 8.10; N, 8.41.

Synthesis of 2: To a suspension of 1,3-(tBu$_2$PNH)$_2$C$_6$H$_4$ (1.0 g, 4.0 mmol) in toluene (20 ml) was added Ni(COD)$_2$ (220 mg, 0.8 mmol) under an argon atmosphere, and the mixture was stirred and heated at 80° C. for 12 h, then cooled to room temperature. The pale yellow solid 2 thus obtained was filtered and washed with pentane (3×3mL), then dried under vacuum (1.5 g, 85%). IR (neat, cm$^{-1}$): ν=1866 (Ni—H), 3353 (NH); $^1$H NMR (400 MHz, C$_6$D$_6$): δ 6.95 (t, J=7.2 Hz, 1H), 6.71 (s, 1H), 5.22 (s, 1H), 4.03 (s, 1H), 1.49 (s, 18H), 1.04 (s, 18H), −15.9 (t, J=56.0 Hz, 1H); $^{13}$C NMR (DMF-d$_7$, 100 MHz): δ 172.9 (dd, J=9.5, 4.7 Hz), 138.6, 128.8, 102.8 (d, J=25.0 Hz), 87.4 (d, J=9.5 Hz), 36.5, 36.3, 28.5; $^{31}$P NMR (162 MHz, C$_6$D$_6$): δ 82.7 (d, J=217.1 Hz, 1P), 74.8 (d, J=217.1 Hz, 1P); HRMS (ESI) Calcd. for C$_{21}$H$_{42}$N$_3$NiP$_2$ requires (M+H$^+$) 456.2207, Found: 456.2201. Elemental analysis (%) for C$_{21}$H$_{41}$N$_3$NiP$_2$: Calc. C, 55.29; H, 9.06; N, 9.21. Found: C, 55.21; H, 8.96; N, 9.02.

Synthesis of 3: To a solution of 2 (1.0 g, 2.2 mmol) in toluene (22 mL) were added KOtBu (494 mg, 4.4 mmol) and MeI (625 mg, 0.28 mL, 4 mmol). The mixture was refluxed for 12 h, which was filtered after the mixture was cooled to room temperature. The volume of the orange filtrate was reduced to 5 mL, and then pentane was added to cause precipitation. The product was collected by filtration, washed with pentane (3×3mL), and dried under vacuum to give an yellow powder of 3 (722 mg, 70% yield). IR (neat, cm$^{-1}$): v=1871 (Ni—H); $^1$H NMR (400 MHz, C$_6$D$_6$): δ 7.01 (t, J=7.2 Hz, 1H), 6.80 (d, J=7.2, 1H), 5.04 (d, J=7.2 Hz, 1H), 2.55 (s, 3H), 1.51 (s, 9H), 1.48 (s, 9H), 1.18 (s, 9H), 1.15 (s, 9H), −15.6 (dd, J=60.8, 45.6 Hz, 1H); $^{13}$C NMR (C$_6$D$_6$, 100 MHz): δ 173.2 (dd, J=9.5, 3.5 Hz), 161.7 (dd, J=13.8, 6.9 Hz), 138.1, 106.9 (d, J=21.5 Hz), 86.0 (d, J=7.7 Hz), 38.1 (d, J=1.7 Hz), 38.0 (d, J=1.7 Hz), 36.6 (d, J=4.3 Hz), 36.4 (d, J=5.2 Hz), 36.3, 30.1, 30.0, 29.0, 28.9; $^{31}$P NMR (162 MHz, C$_6$D$_6$): δ 91.8 (dd, J=224.9, 17.7 Hz, 1P), 83.9 (dd, J=224.9, 25.3 Hz, 1P); HRMS (ESI) Calcd. for C$_{22}$H$_{43}$N$_3$NiP$_2$ requires (M+H$^+$) 470.2364, Found: 470.2338; Elemental analysis (%) for C$_{22}$H$_{42}$N$_3$NiP$_2$: Calc. C, 56.19; H, 9.22; N, 8.94. Found: C, 56.26; H, 9.21; N, 8.91.

General procedures for hydrosilylation of aldehyde: to a flame-dried Schlenk flask was added a solution of nickel PN$^3$P-pincer complex 2 (1.0 mg, 2 μmol) in toluene (1.0 mL), an aldehyde substrate (1.0 mmol) and PhSiH$_3$ (49 μL, 0.4 mmol) under an argon atmosphere. The resulting mixture was stirred at 80° C. until there was no aldehyde left (monitored by withdrawing aliquots and analyzing their $^1$H NMR spectra). The reaction was then quenched by a 10% aqueous solution of NaOH (about 1.0 mL) with vigorous stirring for more than 12 hours. The solution containing the alcohol product was extracted with diethyl ether three times, dried over anhydrous Na$_2$SO$_4$, and concentrated under vacuum. The desired alcohol was further purified by flash column chromatography.

General procedures for reduction of CO$_2$ to methanol: to a fresh vial was added nickel PN$^3$P-pincer complex 2 (4.6 mg, 0.01 mmol), and 1.8 mL of DMF was introduced. The vial was sealed, and CO$_2$ was introduced into the vial via a balloon. The reaction was allowed to stir for 30 min at room temperature, after which diphenylsilane (0.19 mL, 1 mmol) was introduced. The reaction was quenched after 18 h by adding 2 equivalents of NaOH/H$_2$O solution. It was stirred for another 24 h before an aliquot of isopropyl alcohol was added as an internal standard. An aliquot of 0.2 mL was removed from the sample and diluted with dichloromethane before the resulting mixture was subjected to GC analysis.

General procedure for trifluoromethylation of benzaldehyde: to benzaldehyde (0.11 g, 1.0 mmol) in a dry flask under Ar were added DMF (anhydrous, 1 mL), TMSCF$_3$ (0.4 g, 2.8 mmol), and nickel PN$^3$P-pincer complex 2 (9.1 mg, 0.02 mmol). The mixture was stirred at room temperature for 5 h. HCl solution (2N, 1 mL) was added and the solution was stirred at room temperature until all TMS protected intermediate converted to product. Water (6 mL) was added and aqueous layer was extracted with ether (4 mL×3). Organic layers were combined and washed with saturated NaHCO$_3$ aqueous solution (3 mL), brine (3 mL), dried over MgSO$_4$. Solvents were removed under vacuum to the crude residue, which was purified by silica flash chromatography (30% ethyl actate/hexanes) to give 149 mg product (85% yield).

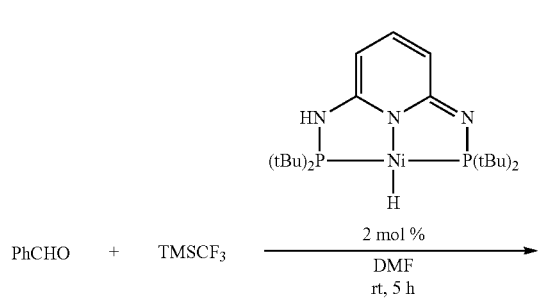

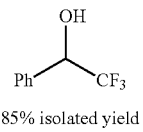

85% isolated yield

General procedure for cycloaddition of CO$_2$ to epoxide: a mixture of the styrene oxide (0.5 mL, 4.4 mmol) and the nickel PN$^3$P-pincer complex 2 (0.09 mmol, 41 mg) was charged in a dry flask; then CO$_2$ was introduced (1 bar) and the mixture was heated at 100° C. for 48 h. The reaction mixture was then cooled to room temperature, methylene chloride was added and the product was purified over silica gel column (20% ethyl actate/hexanes).

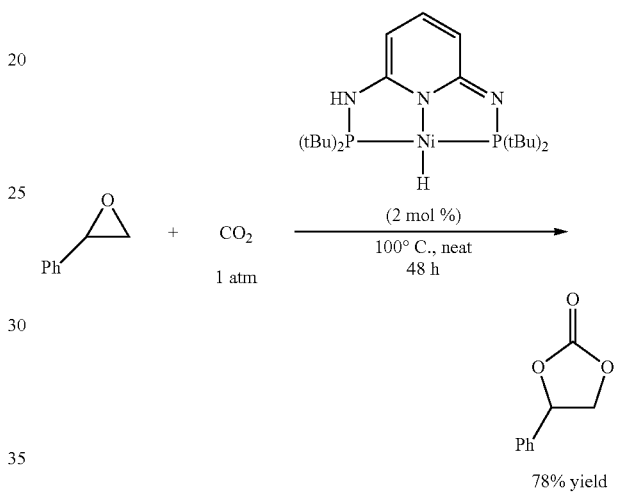

78% yield

General procedure for amide synthesis from alcohols and amines: in an argon-filled glovebox, a 10 mL oven-dried Schlenk tube was charged with nickel PN$^3$P-pincer complex 2 (0.025 mmol, 11 mg), KO$^t$Bu (0.075 mmol, 8.4 mg), and 0.6 mL of toluene. The Schlenk tube was then taken out, and benzylalcohol (0.50 mmol, 54 mg) and benzylamine (0.55 mmol, 59 mg) were added. The reaction mixture was heated to reflux under a flow of argon to facilitate removal of hydrogen for 24 hours before being cooled to room temperature. All the volatiles were removed under vacuum. Purification of the crude product by flash chromatography afforded amide, which was identified by spectral comparison with literature data.

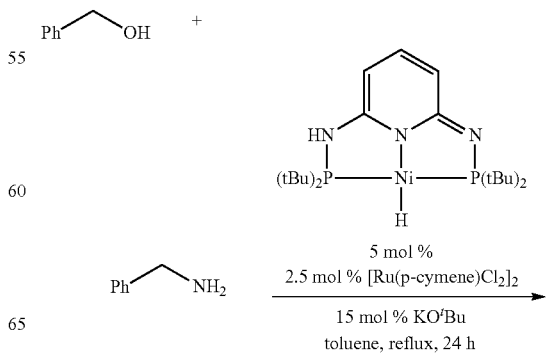

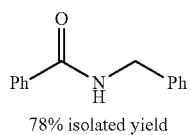

78% isolated yield

Generally the ligands and complexes can be prepared by the methods described in U.S. patent Ser. No. 13/528,481, filed on Jun. 6, 2012, entitled "Phospho-amino Pincer-Type Ligands and Catalytic Metal Complexes Thereof", U.S. Provisional Patent Application No. 61/499,028, filed June 20, 2011, and "Efficient transfer hydrogenation reaction Catalyzed by a dearomatized PN³P ruthenium pincer complex under base-free Conditions", Journal of Organometallic Chemistry, 700 (2012) 202-206, "A sustainable catalytic pyrrole synthesis", Nature Chemistry Vol. 5, 2013, 140-144 and Z. anorg. allg. Chem. 545 (1987) 83-97, the contents of which are incorporated herein by reference in their entirety.

Although the present invention has been described with reference to preferred embodiments, persons skilled in the art will recognize that changes may be made in form and detail without departing from the spirit and scope of the invention. All references cited throughout the specification, including those in the background, are incorporated herein in their entirety. Those skilled in the art will recognize, or be able to ascertain, using no more than routine experimentation, many equivalents to specific embodiments of the invention described specifically herein. Such equivalents are intended to be encompassed in the scope of the following claims.

REFERENCES

The following references to the extent that they provide exemplary procedural or other details supplementary to those set forth herein, are specifically incorporated herein by reference.

1 Crabtree, R. H. *The Organometallic Chemistry of the Transition Metals.* 5th edn, (Wiley, 2009).

2 Hartwig, J. *Organotransition Metal Chemistry: From Bonding to Catalysis.* 1st edn, (University Science books, 2009).

3 Dalko, P. I. & Moisan, L. In the Golden Age of Organocatalysis. *Angewandte Chemie, International Edition* 43, 5138-5175, (2004).

4 Enders, D., Niemeier, O. & Henseler, A. Organocatalysis by N-Heterocyclic Carbenes. *Chemical Reviews (Washington, DC, United States)* 107, 5606-5655, (2007).

5 Grondal, C., Jeanty, M. & Enders, D. Organocatalytic cascade reactions as a new tool in total synthesis. *Nature chemistry* 2, 167-178, (2010).

6 Bugaut, X. & Glorius, F. Organocatalytic umpolung: N-heterocyclic carbenes and beyond. *Chemical Society Reviews* 41, 3511-3522, (2012).

7 Taylor, J. E., Bull, S. D. & Williams, J. M. J. Amidines, isothioureas, and guanidines as nucleophilic catalysts. *Chemical Society Reviews* 41, 2109-2121, (2012).

8 Gruetzmacher, H. Cooperating ligands in catalysis. *Angewandte Chemie, International Edition* 47, 1814-1818, (2008).

9 Milstein, D. Discovery of Environmentally Benign Catalytic Reactions of Alcohols Catalyzed by Pyridine-Based Pincer Ru Complexes, Based on Metal-Ligand Cooperation. *Topics in Catalysis* 53, 915-923, (2010).

10 Gunanathan, C. & Milstein, D. Bond activation by metal-ligand cooperation: design of green catalytic reactions based on aromatization-dearomatization of pincer complexes. *Topics in Organometallic Chemistry* 37, 55-84, (2011).

11 Gunanathan, C. & Milstein, D. Metal-Ligand Cooperation by Aromatization-Dearomatization: A New Paradigm in Bond Activation and "Green" Catalysis. *Accounts of Chemical Research* 44, 588-602, (2011).

12 Ikariya, T. Chemistry of concerto molecular catalysis based on the metal/NH bifunctionality. *Bulletin of the Chemical Society of Japan* 84, 1-16, (2011).

13 Gelman, D. & Musa, S. Coordination Versatility of sp3-Hybridized Pincer Ligands toward Ligand-Metal Cooperative Catalysis. *ACS Catalysis* 2, 2456-2466, (2012).

14 Riduan, S. N., Zhang, Y. & Ying, J. Y. Conversion of Carbon Dioxide into Methanol with Silanes over N-Heterocyclic Carbene Catalysts. *Angewandte Chemie-International Edition* 48, 3322-3325, (2009).

15 Song, J. J.; Tan, Z.; Reeves, J. T.; Gallou, F.; Yee, N. K. & Senanayake, C. H. N-Heterocyclic Carbene Catalyzed Trifluoromethylation of Carbonyl Compounds. *Org. Lett.* 7, 2193-2196 (2005).

16 16 Barbarini, A.; Maggi, R.; Mazzacani, A.; Mori, G.; Sartoria, G. & Sartorioa, R. Cycloaddition of $CO_2$ to epoxides over both homogeneous and silica-supported guanidine catalysts. Tetrahedron Lett. 44, 2931-2934 (2003).

17 Ghosh, S. C. & Hong, S. H. Simple $RuCl_3$-Catalyzed Amide Synthesis from Alcohols and Amines, *Eur. J. Org. Chem.*, 4266-4270 (2009).

18 He, L.-P., Chen, T., Xue, D.-X., Eddaoudi, M. & Huang, K.-W. Efficient transfer hydrogenation reaction Catalyzed by a dearomatized PN3P ruthenium pincer complex under base-free Conditions. *Journal of Organometallic Chemistry* 700, 202-206, (2012).

19 Chen, T. et al. Ruthenium(II) pincer complexes with oxazoline arms for efficient transfer hydrogenation reactions. *Tetrahedron Letters* 53, 4409-4412, (2012).

20 Zeng, G. et al. A Green Approach to Ethyl Acetate: Quantitative Conversion of Ethanol through Direct Dehydrogenation in a Pd—Ag Membrane Reactor. *Chem. Eur. J.* 18, 15940-15943, (2012).

21 He, L.-P., Chen, T., Gong, D., Lai, Z. & Huang, K.-W. Enhanced Reactivities toward Amines by Introducing an Imine Arm to the Pincer Ligand: Direct Coupling of Two Amines To Form an Imine Without Oxidant. *Organometallics* 31, 5208-5211, (2012).

22 Benito-Garagorri, D. et al. Achiral and Chiral Transition Metal Complexes with Modularly Designed Tridentate PNP Pincer-Type Ligands Based on N-Heterocyclic Diamines. *Organometallics* 25, 1900-1913, (2006).

23 Schirmer, W., Floerke, U. & Haupt, H. J. Preparation, properties, and molecular structures of a rigid tridentate chelate ligand N,N'-bis(diphenylphosphino)-2,6-diaminopyridine with MII and M0 transition metals [MII=nickel, palladium, platinum; M0=chromium, molybdenum, tungsten]. *Zeitschrift fuer Anorganische und Allgemeine Chemie* 545, 83-97, (1987).

24 Chakraborty, S., Krause, J. A. & Guan, H. Hydrosilylation of Aldehydes and Ketones Catalyzed by Nickel PCP-Pincer Hydride Complexes. *Organometallics* 28, 582-586, (2009).

25 Jurkauskas, V., Sadighi, J. P. & Buchwald, S. L. Conjugate reduction of alpha,beta-unsaturated carbonyl compounds catalyzed by a copper carbene complex. *Organic Letters* 5, 2417-2420, (2003).

26 Mitton, S. J. & Turculet, L. Mild Reduction of Carbon Dioxide to Methane with Tertiary Silanes Catalyzed by Platinum and Palladium Silyl Pincer Complexes. *Chem. Eur. J.* 18, 15258-15262, (2012).

27 Park, S., Bezier, D. & Brookhart, M. An Efficient Iridium Catalyst for Reduction of Carbon Dioxide to Methane with Trialkylsilanes. *J. Am. Chem. Soc.* 134, 11404-11407, (2012).

28 Heldebrant, D. J., Jessop, P. G., Thomas, C. A., Eckert, C. A. & Liotta, C. L. The Reaction of 1,8-Diazabicyclo [5.4.0]undec-7-ene (DBU) with Carbon Dioxide. *J. Org. Chem.* 70, 5335-5338, (2005).

What is claimed is:

1. A complex comprising a ligand and a metal or metal ion, M, wherein the ligand is a compound according to formula (I), or a deprotonated version thereof, and the ligand is associated with the metal or metal ion, M,

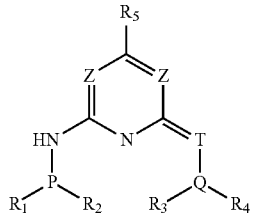

(I)

wherein $R_1$ and $R_2$ are each independently an optionally substituted alkyl$_{(C\leq 12)}$, an optionally substituted aryl$_{(C\leq 12)}$, or an optionally substituted aralkyl$_{(C\leq 12)}$ $R_3$, and $R_4$, if present, are each independently an optionally substituted alkyl$_{(C\leq 12)}$, an optionally substituted aryl$_{(C\leq 12)}$, or an optionally substituted aralkyl$_{(C\leq 12)}$ $R_5$ is a hydrogen atom or an optionally substituted alkyl$_{(C\leq 12)}$, an optionally substituted aryl$_{(C\leq 12)}$, an optionally substituted aralkyl$_{(C\leq 12)}$, an optionally substituted amino, a hydroxyl, or an optionally substituted alkoxyl;

each Z, independently, is $CR_6$ or CH, wherein at least one Z is CH;

$R_6$ is a hydrogen atom or an optionally substituted alkyl$_{(C\leq 12)}$, an optionally substituted aryl (C≤12), an optionally substituted aralkyl (C≤12), an optionally substituted amino, hydroxyl, or an optionally substituted alkoxyl;

T is N;

Q is P; and

M is nickel (Ni), a nickel ion, or a nickel salt, wherein M is attached to X and wherein X is H.

2. The complex of claim 1, wherein $R_1$, $R_2$, $R_3$, and $R_4$ are each an alkyl(C2-10) and $R_5$ is a hydrogen atom.

3. The complex of claim 2, wherein $R_1$, $R_2$, $R_3$, and $R_4$ are each a $C_4$ alkyl.

4. The complex of claim 1, wherein $R_1$, $R_2$, $R_3$, and $R_4$ are each a tert-butyl group.

5. The complex of claim 1, wherein $R_5$ is a hydrogen atom.

6. A catalyst comprising the complex of claim 1, wherein the catalyst is used for at least one of the following:
   (a) converting a carbon dioxide into an alcohol;
   (b) converting an aldehyde into an alcohol;
   (c) trifluoromethylation of benzaldehyde;
   (d) cycloaddition of $CO_2$ to epoxide; and
   (e) amide synthesis from alcohol and amine.

* * * * *